United States Patent [19]

Yamaguchi et al.

[11] Patent Number: 5,006,470
[45] Date of Patent: Apr. 9, 1991

[54] HUMAN MONOCLONAL ANTIBODIES TO CELL SURFACE ANTIGENS OF MELANOMA

[75] Inventors: Hiroshi Yamaguchi, Bronx; Koichi Furukawa; Philip O. Livingston, both of New York; Kenneth O. Lloyd, Bronx, all of N.Y.; Herbert F. Oettgen, New Canon, Conn.; Lloyd J. Old, New York, N.Y.; Sheila R. Fortunato, Hollis, N.Y.

[73] Assignee: Sloan-Kettering Institute for Cancer Research, New York, N.Y.

[21] Appl. No.: 39,479

[22] Filed: Apr. 16, 1987

[51] Int. Cl.$^5$ ............... C12N 5/12; C07K 15/28; A61K 39/00; G01N 33/53

[52] U.S. Cl. ............... 424/85.8; 530/387; 530/388; 424/85.91; 435/240.27; 435/70.21; 435/948; 436/548; 935/96; 935/100; 935/104; 935/107; 935/110

[58] Field of Search ............... 530/387, 388; 435/240.27, 68, 948; 424/85, 85.8; 436/548; 935/96, 100, 104, 107, 110

[56] References Cited

U.S. PATENT DOCUMENTS

| | | | |
|---|---|---|---|
| 4,485,093 | 11/1984 | Runge | 424/85 |
| 4,507,391 | 3/1985 | Pukel et al. | |
| 4,562,160 | 12/1985 | Real et al. | 436/539 |
| 4,642,291 | 2/1987 | Cairncross et al. | |
| 4,675,287 | 6/1987 | Reisfeld et al. | 435/7 |
| 4,677,070 | 6/1987 | Larrick et al. | 435/240 |
| 4,798,790 | 1/1988 | Thomson et al. | |

OTHER PUBLICATIONS

Cheresh, D. A., "Localization of the Gangliosides GD$_2$ and GD$_3$ in Adhesion Plaques and on the Surface of Human Melanoma Cells," *Proc. Nat'l. Acad. Sci.* 81:5767-5771, Sep. 1984.

Shichijo, S. et al., "Inhibitory Effects of Gangliosides on Immune Reactions of Antibodies to Neutral Glycolipids in Liposomes," *Biochim. Biophys. Acta* 858:118-24, 1986.

Livingston, P. O. et al., "Serological Response of Melanoma Patients Receiving Melanoma Cell Vaccines. I. Autologous Cultured Melanoma Cells," *Int. J. Cancer* 30:413-422, 1982.

Kozbor, D. et al., "Human Anti-Tetanus Toxoid Monoclonal Antibody Secreted by EBV-Transformed Human B Cells Fused with Murine Myeloma," *Hybridoma* 1(3):323-328, 1982.

Kundu, S. K. et al., "Binding of Monoclonal Antibody A2B5 to Gangliosides," *Biochem. Biophys. Res. Commun.* 116(3):836-842, Nov. 15, 1983.

Hirabayashi, Y. et al., Biochemistry of Melanoma-Associated Ganglioside Antigens, Chem. Abstracts: 105: 22698 (1986).

Hirabayashi, Y. et al., Syngeneic Monoclonal-Antibody against Melanoma Antigen with Interspecies Cross-Reactivity Recognizes Gm$_3$, a Prominent Ganglioside of Melanoma, J. Bio. Chem. 260: 13328-13333 (1985).

Houghton, A. et al., Detection of Cell Surface and Intracellular Antigens by Human Monoclonal Antibodies, J. Exp. Med. 158: 53-65 (1983).

Steinitz, M. et al., E.B. Virus-Induced B Lymphocyte Cell Lines Producing Specific Antibody, Nature 269: 420-422 (1977).

*Primary Examiner*—Margaret Moskowitz
*Assistant Examiner*—Paula Hutzell
*Attorney, Agent, or Firm*—John P. White

[57] ABSTRACT

This invention provides a monoclonal antibody, produced by the hybridoma cell line designated GXM1, which specifically binds to a human class 1tumor antigen. This invention also provides a human monoclonal antibody, produced by a hybridoma cell line designated HJM1, which specifically binds to each of the ganglioside antigens GD2, GD3, GM3 and GD1b. This invention further provides a human monoclonal antibody, produced by a hybridoma cell line designated FCM1, which specifically binds to the ganglioside antigens GM3 and GD1a. Finally, this invention provides a human monoclonal antibody, produced by a hybridoma cell line designated DSM1, which specifically binds to a human class 2 tumor protein antigen.

14 Claims, 6 Drawing Sheets

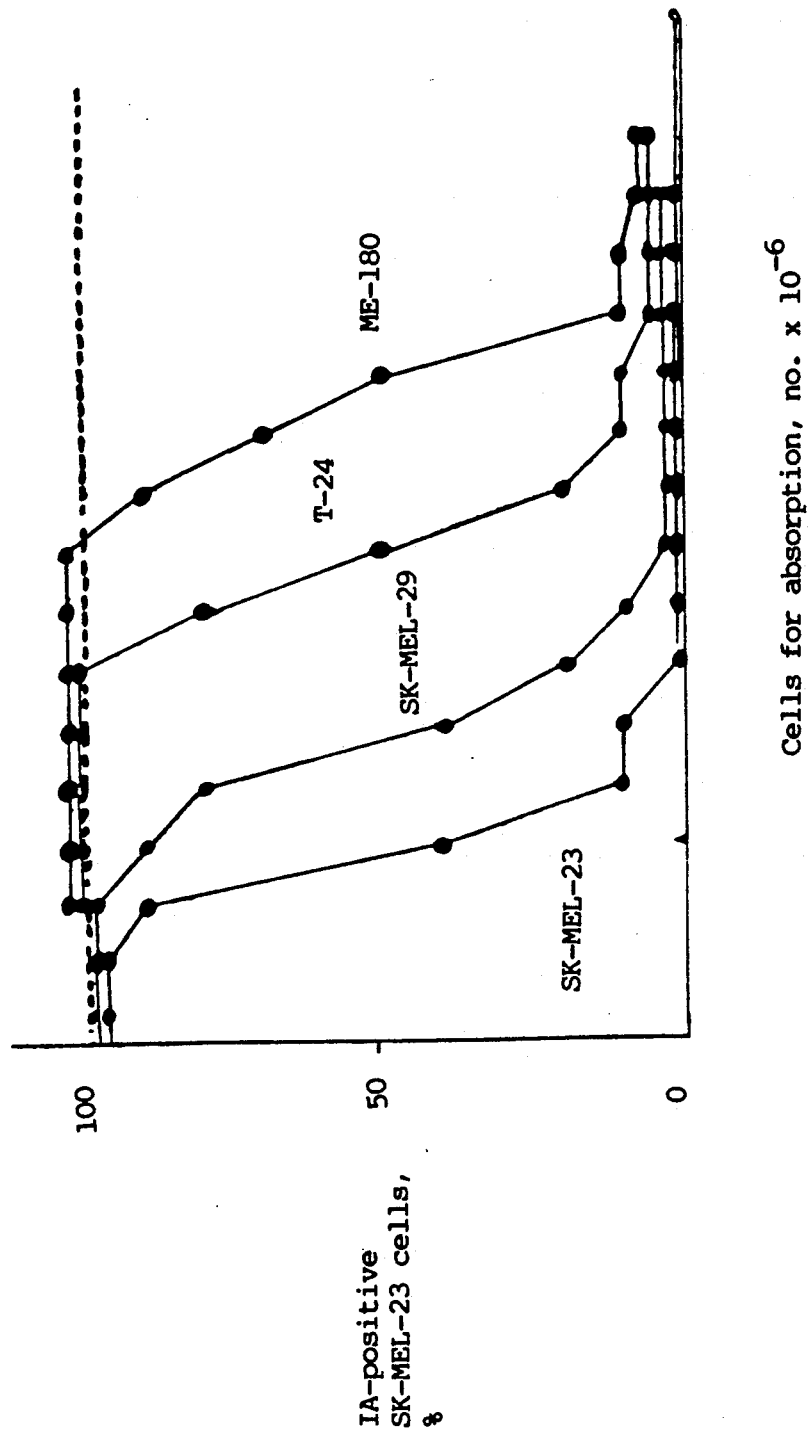
Figure 1-A

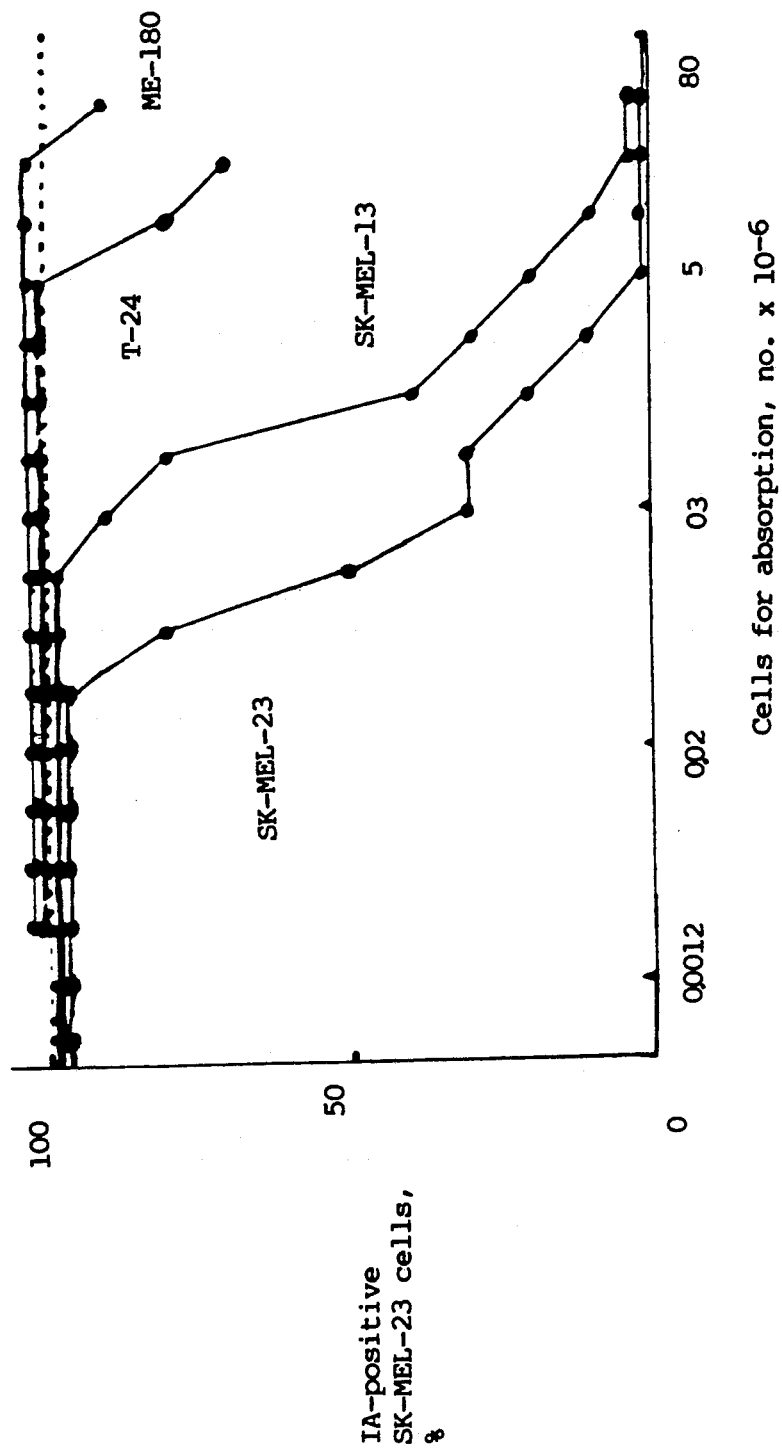
Figure 1 - B

HUMAN MONOCLONAL ANTIBODIES TO CELL SURFACE ANTIGENS OF MELANOMA

This invention was made with government support under Grant Numbers CA-33049 and CA-08748 from the National Cancer Institute. The U.S. Government has certain rights in the invention.

BACKGROUND OF THE INVENTION

Throughout this application, various publications are referenced by arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

There is accumulating evidence that melanoma is an immunogenic cancer in humans. In addition to indirect indications such as spontaneous regressions, lymphoid infiltrates, and increased incidence of melanoma in immunosuppressed patients, several groups have reported specific humoral and cellular immune reactions to melanoma cell-surface antigens (1-6). Based on the assumption that an immune restraint to melanoma growth exists and can be strengthened, vaccines containing melanoma-derived antigens are being tested in patients with the disease at several centers (7-9).

Serological methods have been pursued most extensively to define melanoma antigens that are immunogenic in melanoma patients. We have studied the reactivity with surface antigens of cultured melanoma cells from the same patient (termed autologous typing) in more than 200 patients. Three classes of antigens have been defined in this way (2). Class 1 (unique) melanoma antigens are restricted to the autologous melanoma; six examples of class 1 antigens have been detected (10-15). Class 2 melanoma antigens are detected on the autologous melanoma, on a subset of allogeneic melanoma cells, and on other neuroectodermally derived tumors; these class 2 antigens have characteristics of autoimmunogenic differentiation antigens, and one of the best-analyzed class 2 melanoma antigens is the ganaglioside GD2 (16). Class 3 melanoma antigens are not restricted to any differentiation lineage and are more widely distributed.

The advent of methods for producing human monoclonal antibodies (mAbs) through immortalizing human lymphocytes with Epstein-Barr virus (EBV) (17) or by fusion with human or mouse lymphoblastoid/myeloma partners (18) provides a new level of precision in the analysis of the immune response to melanoma.

Additionally, antibodies for melanoma patients reacting with melanoma cell surfaces or intracellular antigens have been isolated (19-24).

SUMMARY OF THE INVENTION

This invention provides a monoclonal antibody which specifically binds to a human class 1 tumor antigen. The invention also provides for the hybridoma cell line designated GXM1 which produces the human monoclonal antibody.

This invention also provides for a human monoclonal antibody which specifically binds to each of the ganglioside antigens GD2, GD3, GM3 and GD1b. Additionally, this invention provides for a hybridoma cell line designated HJM1 which produces the human monoclonal antibody.

This invention also provides for a human monoclonal antibody which specifically binds to the ganglioside antigens GM3 and GD1a. Additionally, this invention provides for a hybridoma cell line designated FCM1 which produces the human monoclonal antibody.

This invention also provides for a human monoclonal antibody which specifically binds to a human class 2 tumor protein antigen. Additionally, this invention provides for a hybridoma cell line designated DSM1 which produces the human monoclonal antibody.

This invention also provides a method of in vitro melanoma diagnosis. The method comprises contacting a sample from a human subject with a monoclonal antibody labeled with a detectable moiety under suitable conditions so as to form a complex between the monoclonal antibody and an antigen derived from the melanoma and detecting the complex so formed, thereby diagnosing melanoma in the subject.

This invention also provides a method of in vivo melanoma diagnosis. The method comprises administering to a human subject a suitable amount of a monoclonal antibody labeled with a detectable moiety under suitable conditions so as to allow the monoclonal antibody to form a complex with a melanoma surface antigen and detecting the complex so formed, thereby diagnosing melanoma in the subject.

This invention also provides a conjugate comprising monoclonal antibodies of this invention attached to a cytotoxic tumor agent. This invention further provides a therapeutic composition comprising an effective melanoma growth inhibiting amount of the conjugate and a pharmaceutically acceptable carrier.

Finally, this invention provides a method of treating melanoma in a human subject. The method comprises administering to the subject an effective therapeutic amount of the monoclonal antibodies of this invention or the composition of the monoclonal antibody-cytotoxic tumor agent complex.

BRIEF DESCRIPTION OF THE FIGURES

FIGS. 1A and 1B show the quantitative absorption analysis of human mAb HJM1. Comparative absorption capacity of cells harvested by mechanical scraping (cell viability, 30%) (A) or trypsinization (cell viability, 95%) (B). In direct serological tests, SK-MEL-13, 23, and 29 showed titers of 1:32 to 1:1024, whereas T-24 and ME-180 were not reactive. IA, immune adherence. Dashed line, unabsorbed HJM1 supernatant.

DETAILED DESCRIPTION OF THE INVENTION

Figure 2:
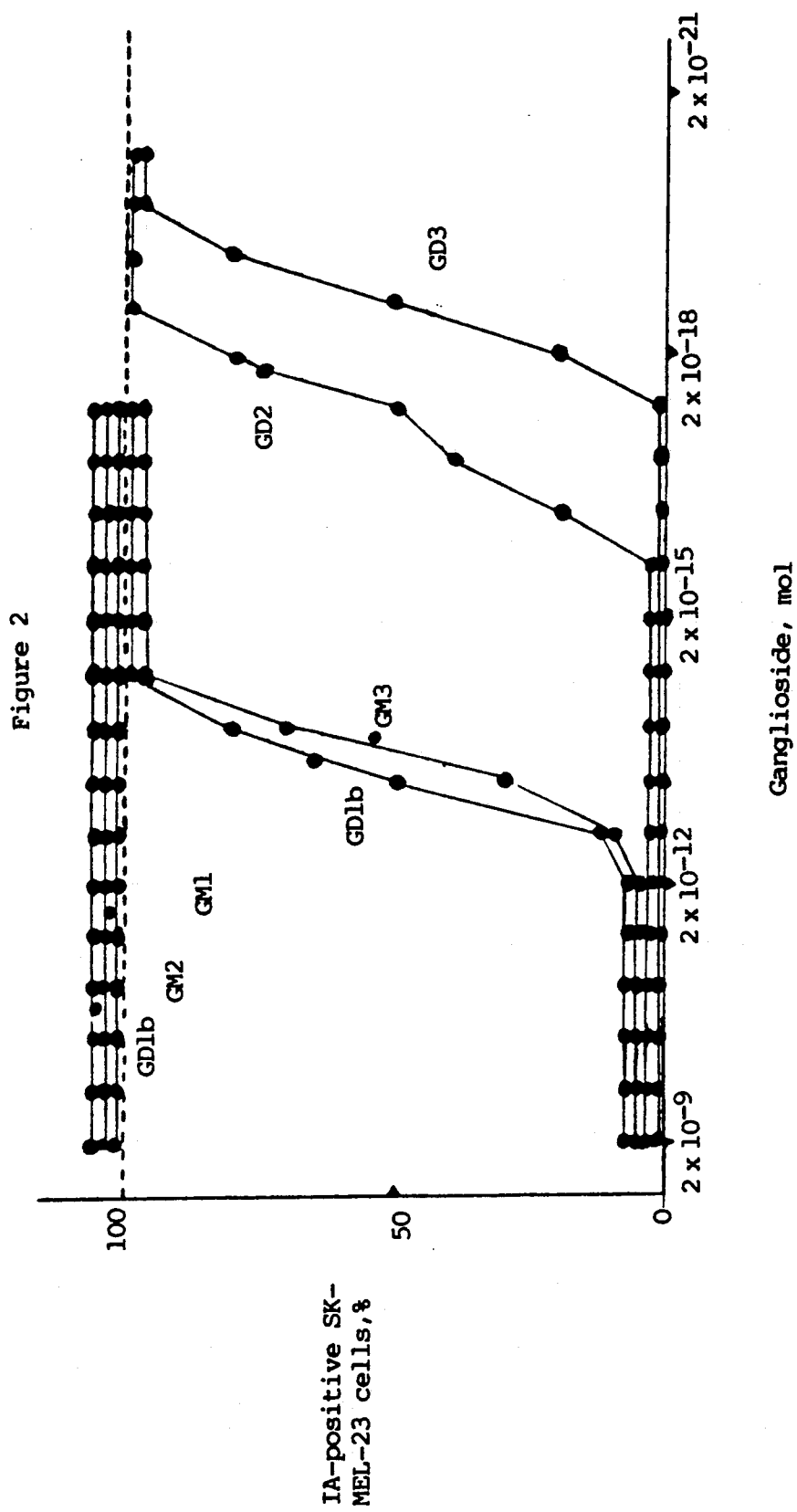
FIG. 2 shows antibody inhibition tests of human mAb HJM1 with purified gangliosides. The dashed line represents the uninhibited HJM1 supernatant.

This invention provides a monoclonal antibody which specifically binds to a human class 1 tumor antigen. The monoclonal antibody may be a murine monoclonal antibody or a human monoclonal antibody. The invention also provides the hybridoma cell line designated GXM1 which produces the human monoclonal antibody.

This invention also provides a human monoclonal antibody which specifically binds to each of the ganglioside antigens GD2, GD3, GM3 and GD1b. Additionally, this invention provides a hybridoma cell line designated HJM1 which produces the human monoclonal antibody.

This invention further provides a human monoclonal antibody which specifically binds to the ganglioside antigens GM3 and GD1a. Additionally, this invention provides for a hybridoma cell line designated FCM1 which produces the human monoclonal antibody.

This invention still further provides a human monoclonal antibody which specifically binds to a human class 2 tumor protein antigen. Additionally, this invention provides for a hybridoma cell line designated DSM1 which produces the human monoclonal antibody.

The monoclonal antibodies of this invention may be labeled with a detectable moiety.

This invention also provides a method of in vitro melanoma diagnosis. The method comprises contacting a sample from a human subject with a monoclonal antibody labeled with a detectable moiety under suitable conditions so as to form a complex between the monoclonal antibody and an antigen derived from the melanoma and detecting the complex so formed, thereby diagnosing melanoma in the subject. Merely by way of example, the sample from a human subject may comprise a tissue sample, sera, urine, cerebro-spinal fluid, amniotic fluid, sputum, lung lavage, ascites fluid, saliva or any mucus type body secretion.

This invention also provides a method of in vivo melanoma diagnosis. The method comprises administering to a human subject a suitable amount of a monoclonal antibody labeled with a detectable moiety under suitable conditions so as to allow the monoclonal antibody to form a complex with a melanoma surface antigen and detecting the complex so formed, thereby diagnosing melanoma in the subject.

This invention further provides a conjugate comprising monoclonal antibodies of this invention attached to a cytotoxic tumor agent. This invention further provides a therapeutic composition comprising an effective melanoma growth inhibiting amount of the conjugate and a pharmaceutically acceptable carrier. The growth inhibiting amount may be an amount sufficient to kill the melanoma. Merely by way of example, suitable pharmaceutically acceptable carriers may include water and buffered saline.

This invention still further provides a method of treating melanoma in a human subject. The method comprises administering to the subject an effective therapeutic amount of the composition of the monoclonal antibody-cytotoxic tumor agent complex.

This invention further provides a therapeutic composition comprising an effective melanoma growth inhibiting amount of a monoclonal antibodies of this invention. Additionally, this invention provides a method of treating melanoma in a human subject which comprises administering to the subject an effective therapeutic amount of the therapeutic composition.

MATERIAL AND METHODS

Tissue Culture. Tumor cell lines were established and maintained as described (10). Several melanoma cell lines (see Table I) were adapted to growth in serum-free insulin (5 micrograms/ml)/transferrin (5 micrograms/ml)/selenium (5 micrograms/ml) (ITS) medium.

Fusion Procedure. Lymph node lymphocytes (LNL) and peripheral blood lymphocytes (PBL) were isolated by Ficoll/Hypaque centrifugation and fused with human LICR-LON-HMy-2 (LICR-2) lymphoblastoid cells or mouse NS-1 myeloma cells as described (19, 25). NS-1 fusions with EBV transformed cells (after two limiting dilution passages of $10^3$–$10^{10}$ cells per passage) or LICR-2 hybrids were performed in the same way as direct lymphocyte fusions, but hybrids were selected by 0.2mM hypoxanthine/0.4 micromolar aminopterin/32 micromolar thymidine (HAT) and 10 micromolar ouabain (Sigma) for the first week and HAT for the second week; this was followed thereafter by culture in RPMI 1640 medium containing 15% fetal bovine serum, 0.2 mM hypoxanthine, and 32 micromolar thymidine.

EBV Transformation. EBV-containing supernatants from the B95-8 marmoset lymphoblastoid cell line (26) were collected and passed through a 0.4 micrometer filter and stored at $-80°$ C. LNL or PBL were suspended in RPMI 1640 medium containing 10% fetal bovine serum and adjusted to $2\times10^6$ cells per ml. Five volumes of lymphocyte cell suspension was mixed with 1 vol of B95-8 supernatant and placed in T-30 flasks (Falcon). After incubation overnight in a 5% $CO_2$ (in air) incubator, cells were washed once, resuspended at $1-4\times10^5$ cells per ml, and plated ($2-8\times10^4$ cells per well) in 96-well tissue culture plates. Wells containing antibody-producing cells were expanded in 24-well tissue culture plates and subsequently subcultured by limiting dilution in 96-well plates.

Serological Assays. Techniques for the detection of cell-surface antigens (11,14) and intracellular antigens (19) have been described. Antigen characterization by heat treatment and neuraminidase treatment was performed as described (27,28). Antibody inhibition tests were carried out by mixing the cell extract or purified gangliosides with culture supernatant (diluted three doubling dilutions below the end point), incubating for 30 min at room temperature, and testing for residual antibody reactivity on SK-MEL-23 target cells.

Glycolipids. Cells were extracted by chloroform/methanol, and neutral and acidic glycolipids were isolated as described (28). GM3 and GD3 were purified and GM2 was prepared as described (29). GM1, GD1a, and GT1 were purchased from Supelco (Bellefonte, PA).

ELISA for glycolipids and immunostaining after TLC were performed as described (28-30).

Generation of Human mAbs. Four approaches to generating human mAbs from the lymphocytes of patients with melanoma were compared (Table I).

TABLE I

Generation of human mAbs from lymphocytes of melanoma patients

| Method/ lymphocyte source | Trials. no. | Wells with growing cells. no./10⁷ lymphocytes Median | (Range) | % Ig+ wells* Median | (Range) | Wells screened for cell-surface reactivity,+ no. | | Positive wells. no. | Stable cultures or clones, no. |
|---|---|---|---|---|---|---|---|---|---|
| LICR-2 fusion | | | | | | | | | |
| LNL | 20 | 11.2 | (1.1–200.0) | 76 | (21–94) | Allo. | 895 | 10 | 3 |
| PBL | 10 | 0 | (0) | | | | | | |
| NS-1 fusion | | | | | | | | | |
| LNL | 12 | 25.2 | (6.3–37.3) | 19 | (3–32) | Allo. | 509 | 5 | 3 |
| PBL | 18 | 0 | (0–27.6) | 0 | (0–8) | Allo. | 21 | 0 | |
| EBV transformation | | | | | | | | | |
| LNL | 13 | 270.0 | (31.0–500.0) | 100 | (56–100) | Allo. | 613 | 18 | 6 |
| | | | | | | Auto. | 1.817 | 8 | 0 |
| PBL | 38 | 300.0 | (33.3–480.0) | 100 | (85–100) | Allo. | 1.899 | 38 | 5 |
| | | | | | | Auto. | 15.288 | 46 | 6 |
| NS-1 fusion | 35 | 5.0 | (0–76.7) | | | | 1.505 | 258 | 8 |

*% of wells with growing cells having Ig in culture supernatants of ≧500 ng/ml.
+Allo. reactivity with allogenic target cells. Auto. reactivity with autologous melanoma cells.
Fusion with EBV-transformed B cells or LICR-2 clones.

Fusion of LNL with mouse NS-1 myeloma cells resulted in a higher yield of clones than fusion with LICR-2. NS-1 hybrids grew more vigorously than LICR-2 hybrids, and this facilitated clonal selection and expansion of NS-1-derived clones. No LICR-2-hybrids were obtained after fusion with PBL, and the frequency of NS-1 hybrids was extremely low with lymphocytes from this source. In contrast to fusion techniques, EBV transformation resulted in an equally high frequency of proliferating cells from LNL and PBL. Testing individual wells for immunoglubulin secretion after initial plating of fused or EBV-transformed lymphocytes indicated that NS-1 or LICR-2 hybrids were clonally derived, producing a single heavy chain class, whereas EBV transformation resulted in polyclonal expansion of B cells with greater than 95% wells containing cells secreting IgM, IgG, and IgA. To identify cells producing antibodies with cell-surface reactivity, supernatants containing greater than or equal to 500 ng of immunoglobulin per ml were allowed to react with a screening panel of 20 different cell lines, including 10 melanomas, 5 leukemias, and 5 epithelial cancers. In 22 cases, autologous melanoma cells from the lymphocyte donor were also available for screening.

As shown in Table I, supernants from 1.1% of wells (10/895) from LICR-2 fusions with LNL contained surface-reactive antibodies; in the case of NS-1 fusions, the figure was 1% (5/509). Three stable antibody-secreting clones were derived from LICR-2 fusions and three were derived from NS-1 fusions. Primary screening of supernatant from EBV-transformed cells identified 2-3% of wells with surface-reactive antibody against allogeneic cells and 0.3-0.4% against autologous cells. Expansion and limiting dilution plating of EBV-transformed cells resulted in a loss greater than 80% of antibody-secreting cultures. However, 17 stable cultures of EBV-transformed cells secreting cell-surface-reactive antibody were derived. To overcome problems of instability and low cloning efficiency of EBV-transformed cultures, we attempted to develop stable NS-1 hybrids of antibody-secreting EBV-transformed cells. The fusion frequency was generally low (5.0 per 10⁷ EBV-transformed cells), but hybrids secreting antibody with the same reactivity as the parental EBV-transformed cultures were obtained in 15/35 attempts. With vigorous subcloning, 8/15 clones retained stable antibody-producing capacity, a frequency similar to our experience in deriving stable NS-1 hybrids in this and past studies (25).

Specific Analysis of Human mAbs. The six human mAbs were chosen for detailed specificity analysis. The pattern of cell-surface reactivity in direct test and absorption analysis with a panel of cultured cells is shown in Table II. Five of the antibodies were produced by NS-1 hybrids with EBV-transformed cells; the other antibody (2.39M) cam from an NS-1-LICR-2 cloned hybrid

TABLE 2

Serological characterization of six human mAbs derived from lymphocytes of melanoma patients

| Cells | GXM1 T | A | HJM1 T | A | FCM1 T | A | DSM1 T | A | 32-27M T | A |
|---|---|---|---|---|---|---|---|---|---|---|
| Melanoma | | | | | | | | | | |
| SK-MEL-13 | — | — | 64 | + | 512 | + | 10,000 | + | 256 | + |
| SK-MEL-23 | — | — | 1024 | + | 1024 | + | — | — | 512 | + |
| SK-MEL-28 | — | — | 64 | + | 128 | + | 40,000 | + | 256 | + |
| SK-MEL-28* | | | 64 | | 256 | | 40,000 | + | — | — |
| SK-MEL-29 | 16 | + | 32 | + | 32 | + | 40,000 | + | 128 | + |
| SK-MEL-31 | — | — | ± | + | 4 | + | 2,560 | + | 1024 | + |
| SK-MEL-37 | — | — | 4 | + | 64 | + | — | + | 32 | + |
| SK-MEL-61 | — | — | 128 | + | 256 | + | 2,560 | + | 32 | + |
| SK-MEL-93-II | — | — | ± | + | 128 | + | 640 | + | 512 | + |
| SK-MEL-93-II* | | | | | | | 640 | + | — | — |
| SK-MEL-94 | — | — | 256 | + | 4096 | + | — | — | 512 | + |
| SK-MEL-130 | — | — | 32 | + | 32 | + | 10,000 | + | 16 | |

TABLE 2-continued

Serological characterization of six human mAbs derived from lymphocytes of melanoma patients

| Cells | GXM1 T | GXM1 A | HJM1 T | HJM1 A | FCM1 T | FCM1 A | DSM1 T | DSM1 A | 32-27M T | 32-27M A |
|---|---|---|---|---|---|---|---|---|---|---|
| SK-MEL-173 | − | − | 64 | + | 256 | + | 10,000 | + | 1024 | + |
| SK-MEL-177 | 2048 | + | − | + | − | + | 2,560 | + | 128 | |
| SK-MEL-177* | 2048 | + | | | | | | | | |
| SK-MEL-189 | − | − | 16 | + | 256 | + | 2,560 | + | 64 | |
| MeWo | − | − | ± | + | 4096 | + | 40,000 | + | 512 | + |
| *Astrocytoma* | | | | | | | | | | |
| SK-MG-1 | − | − | − | | − | | 640 | + | 128 | + |
| SK-MG-4 | − | − | − | + | − | + | 2,560 | + | 256 | + |
| SK-MG-14 | − | − | − | + | − | + | 640 | + | | |
| U-251-MG | − | − | − | + | 8 | + | 6,400 | + | 128 | + |
| SK-MG-3,-11 | | | | | | | 10,000 | + | | |
| SK-MG-21,-23 | | | | | | | − | − | | |
| *Neuroblastoma* | | | | | | | | | | |
| SK-NMC | − | − | − | + | 32 | + | 40,000 | + | 256 | + |
| SK-NSH,1MR-32 | | | | | | | − | − | | |
| *Leukemia* | | | | | | | | | | |
| HL-60 | − | − | − | + | − | + | 2,560 | + | 4 | + |
| K-562 | − | − | − | + | − | + | − | + | − | + |
| CCRF-HSB-2 | − | − | − | + | − | + | − | − | ± | + |
| CCRF-CEM,T-45 | − | − | − | + | − | + | − | − | − | − |
| NALL-1 | − | − | − | + | − | + | − | + | − | − |
| NALM-1 | − | − | − | + | − | + | | | − | − |
| ARA-10 | − | − | − | + | − | + | | + | − | − |
| BALL-1 | − | − | − | + | − | + | | ± | − | − |
| DAUDI,SK-LY-16 | − | − | − | + | − | + | | | | |
| *EBV-transformed B cell* | | | | | | | | | | |
| AH,DS,HJ | − | − | − | + | − | + | | − | − | − |
| FC | − | − | − | + | − | + | | ± | − | − |
| GX | − | − | − | − | − | | | + | − | − |
| *Renal cancer* | | | | | | | | | | |
| SK-RC-6 | − | − | − | + | 32 | + | 2,560 | + | − | − |
| SK-RC-7 | − | − | − | + | 128 | + | 40,000 | + | − | − |
| SK-RC-9 | − | − | − | + | 4096 | + | 40,000 | + | − | − |
| SK-RC-54 | | | | | ± | | 10,000 | + | | |
| SK-RC-45,-48 | | | | | ± | − | − | | | |
| *Bladder cancer* | | | | | | | | | | |
| T-24 | − | − | − | + | − | + | 10,000 | + | − | − |
| 235-J | | | | | | | 40,000 | + | | |
| 5637,Scaber | | | | | | | − | − | | |
| *Lung cancer* | | | | | | | | | | |
| SK-LC-8 | | | | | | | 40,000 | + | | |
| SK-LC-6,-12 | − | − | − | + | − | + | − | − | − | − |
| SK-LC-7 | | | | | | | − | − | | |
| *Breast cancer* | | | | | | | | | | |
| MCF-7 | − | − | − | + | − | + | − | − | − | − |
| MDA-MB-361 | − | − | − | + | 8 | + | − | − | − | − |
| NDA-MB-231 | | | | | 8 | | − | − | | |
| CAMA | | | | | − | | − | − | | |
| SK-BR-5 | | | | | − | | − | + | | |
| *Colon cancer* | | | | | | | | | | |
| HT-29,SW-480 | − | − | − | + | − | + | − | − | − | − |
| SW-403,SW-837 | | | | | − | | − | − | | |
| *Other cancers* | | | | | | | | | | |
| CAPAN-2 | − | − | − | + | − | + | − | − | − | − |
| ME-180 | − | − | − | + | − | + | − | − | − | − |
| SK-OV-3 | − | − | − | + | − | + | − | − | − | − |
| GCC-SV | − | − | − | + | − | + | − | − | − | − |
| PBL(n = 4) | − | − | − | − | − | − | − | − or + | − | − |
| *Fibroblasts* | | | | | | | | | | |
| WI-38 | − | − | − | + | 64 | + | 10,000 | + | 256 | + |
| Adult skin | | | | | | | 2,560 | + | | |
| Melanocytes(n = 3) | − | | − | | 4096 | | − or 2,560 | | − or + | |
| Normal kidney | − | | − | | 128 | | − or | | | |

TABLE 2-continued

Serological characterization of six human mAbs derived from lymphocytes of melanoma patients

| Cells | GXM1 T | GXM1 A | HJM1 T | HJM1 A | FCM1 T | FCM1 A | DSM1 T | DSM1 A | 32-27M T | 32-27M A |
|---|---|---|---|---|---|---|---|---|---|---|
| Epithelium(n = 3) | | | | | | | 40,000 | | | |
| Erythrocytes A,B,AB,O | − | − | − | − | − | − | − | − | − | − |
| Xenogenic cells | | | | | | | | | | |
| JB-RH | − | − | − | + | 4 | + | − | − | − | − |
| Sheep erythrocytes | − | − | − | − | − | − | − | − | 512 | + |

2.39M was tested by the same cell panel used here, and it only reacted with sheep erythrocytes (titer, 1:128). T, titer: sequential dilution (reciprocal) showing 50% erythrocyte-rosetted target cells. −, No reaction in direct tests at a dilution of 1:2; ±, <50% reactivity at a dilution of 1:2; =, results with autologous combinations of antibody and target cells. IgM antibodies were detected by immune adherence assays. DSM1 was treated by PA assays. A, absorption test. Supernatant (diluted according to end point) was absorbed with the indicated cell type and tested for residual activity for SK-MEL-177 (GXM1), SK-MEL-23 (HJM1,FCM1), SK-MEL-13 (DSM1), or MeWo (32-27M) target cells. +, Complete absorption; ±, partial absorption; −, no absorption.
*Cells cultured in serum-free medium containing ITS.

GXM1 is an IgM antibody derived from PBL and which reacts which the patient's own melanoma cell line, SK-MEL-177 (titer, 1/2048). With the exception of autologous melanoma reactivity and low titer reactivity with 1 of the 13 other melanoma cell lines, no other cell type, including autologous PBL or autologous EBV-transformed B cells, reacted in direct tests or absorption analysis. The antigen is heat labile.

Figure 3:
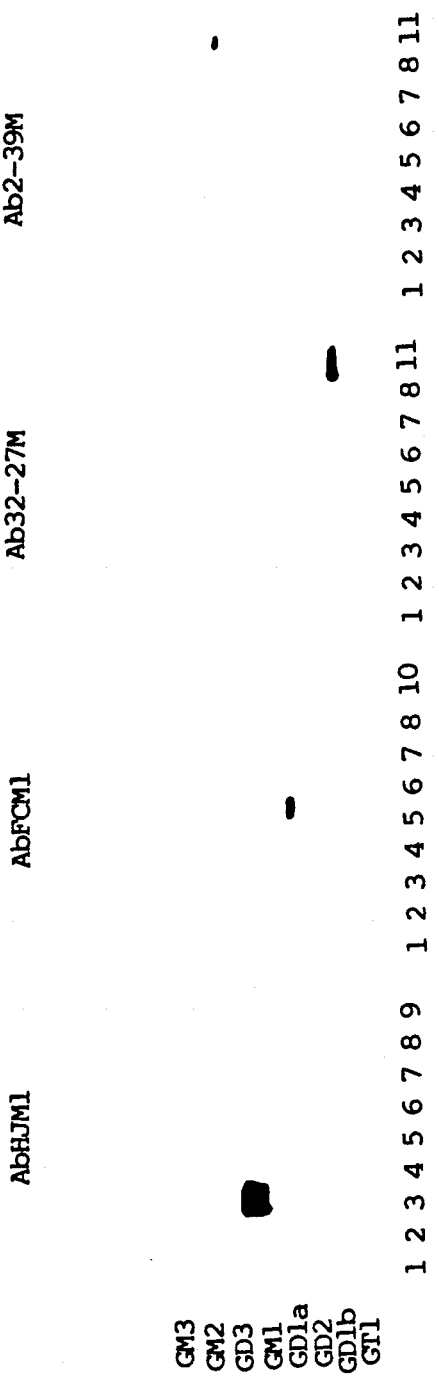
FIG. 3 shows the reactivity of four human mAbs with gangliosides as determined by immunostaining after TLC. Lanes 1-8, purified N-acetyl-type gangliosides. Lanes 1, GM3; lanes 2, GM2; lanes 3, GD3; lanes 4, GM1; lanes 5, GD1$a$; lanes 6, GD2; lanes 7, GD1$b$; lanes 8, GT1; lane 9, ganglioside mixture from cat erythrocytes; lane 10, ganglioside mixture from horse erythrocytes; lanes 11, ganglioside mixture from sheep erythrocytes. Lanes 1-8 contained 1 mmol of ganglioside. The plates were developed with chloroform/methanol/3.5 M NH$_4$OH, 60:35:8, vol/vol. mAbs: hybridoma supernatants (diluted 1:5 to 1:10) were used, except in the case of HJM1, where a 1:5 dilution of EBV-transformed supernatants was used.

HJM1 is an IgM antibody derived from PBL. In direct tests this antibody reacts with 13/14 melanoma cell lines but not with 50 other cell types. Qualitative absorption tests with cells collected by mechanical scraping showed a positive absorption pattern with all cells except erythrocytes. Indirect immunofluorescence (IF) tests with fixed cells to identify cytoplasmic antigen indicated that all nucleated human cells were antigen-positive. To test the possibility that antigen-absorbing cell-surface reactivity was derived from intracellular antigen released by cell damage during collection, we compared the absorbing capacity of cells harvested by scraping (cell viability, less than 30%) and cells harvested by trypsinization (cell viability, greater than 95%) (FIG. 1). In contrast to the results with cells harvested mechanically, absorption tests with trypsinized cells correlated with surface reactivity, i.e., antibody was absorbed with cells having surface expression of the antigen and not absorbed with cells lacking surface expression. The antigen detected by HJM1 is heat-stable and neuraminidase-sensitive, suggesting that it is an acidic glycolipid. Antibody inhibition tests with purified gangliosides showed that HJM1 was strongly inhibited by GD3 and GD2, inhibited less by GD1b and GM3, and not inhibited by GM2, GM1, and GD1a (FIG. 2). Immunostaining of ILC plates confirmed the strong reactivity of HJM1 with GD2 (FIG. 3).

Figure 4:
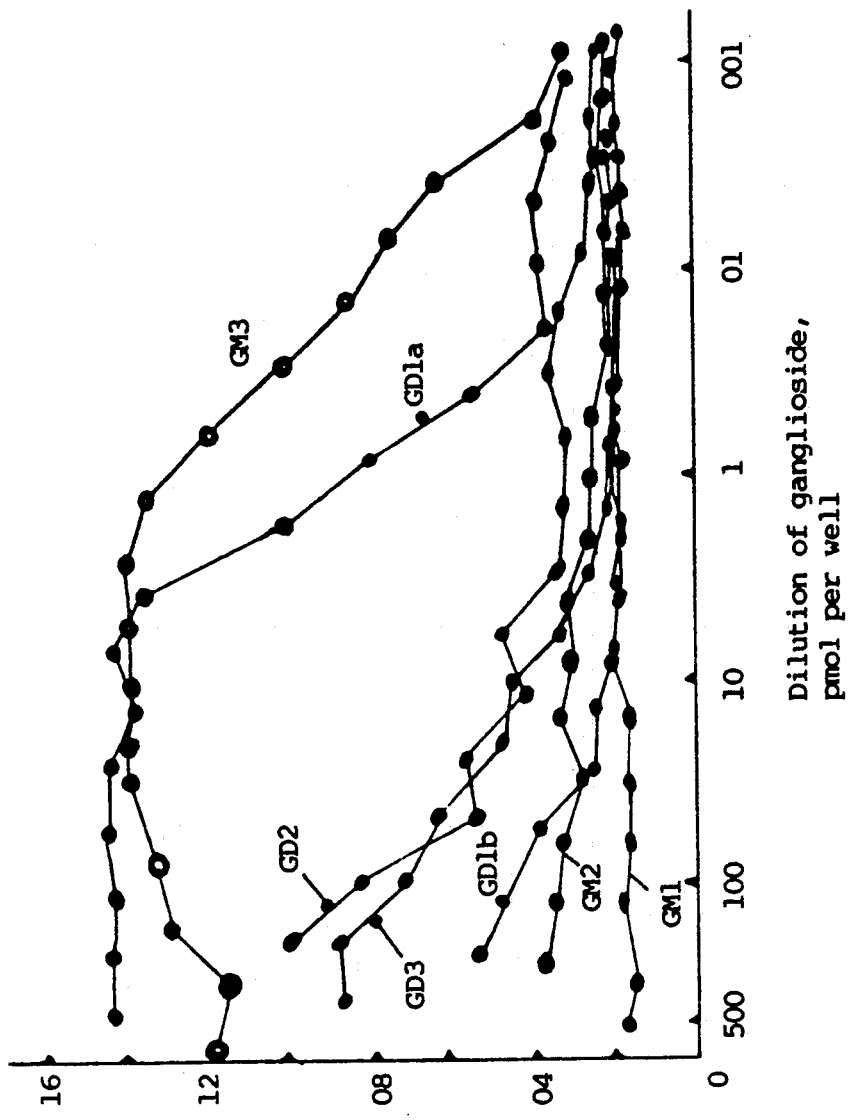
FIG. 4 shows the reactivity of human mAb FCM1 with glycolipids in the ELISA.

FCM1 is an IgM antibody derived from PBL. The reactivity of this antibody in direct tests is broader that HJM1, extending to renal cancer cell lines and melanocytes. Similar to findings with HJM1, absorption and indirect IF tests with fixed cells indicated that all nucleated cells were positive for the FCM1-detected antigen. However, in the case of FCM1, trypsinization did not abolish the absorbing capacity of cells that were not reactive in direct tests, indicating that low levels of surface antigenic expression were detectable by the more sensitive absorption test but not by direct tests. The antigen is heat-stable and neuraminidase-sensitive, suggesting that it is an acidic glycolipid. ELISAs with purified gangliosides showed that FCM1 reacts most strongly with GM3 and GD1a (FIG. 4). Immunostaining of TLC plates confirmed this strong reactivity of FCM1 for GM3 and GD1a (FIG. 3).

DSM1 is an IgG antibody derived from PBL from patients (DS) who had been vaccinated with repeated injections of an allogeneic melanoma cell line, SK-MEL-13, followed by injections of the autologous melanoma cell line (SK-MEL-94). The patient developed protein A (PA) reactivity for the allogeneic melanoma cell line (titer, 1/40,000) but not for the autologous melanoma cell line. DSM1 reacts with 42/85 cell lines in this panel. A comparison of the absorption analysis of DSM1 and high-titered serum from patient DS showed identical results (data not shown), indicating that the mAb has the same specificity as serum antibody. EBV-transformed B cells from the donor of the SK-MEL-13 target cell (AH) did not absorb reactivity from DSM1 or DS serum, suggesting that alloantigenic systems such as HLA, class 1, or class 2 antigens were not involved. The antigen detected by DSM1 is heat-labile, hydrophobic, and binds to Con A.

Figure 5:
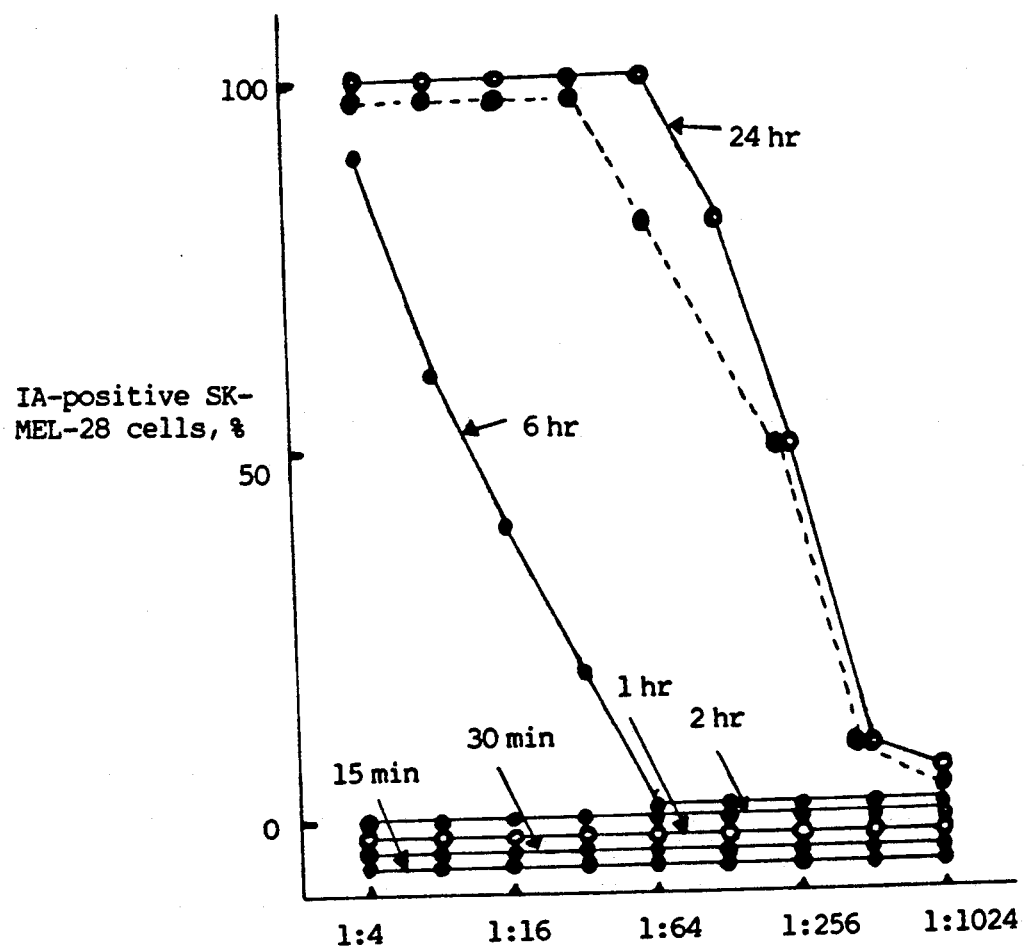
FIG. 5 shows the reconstitution of the 32-27M antigen by culture in fetal bovine serum. SK-MEL-28 cells cultured in ITS medium were preincubated with fetal bovine serum for the indicated times. After incubation, supernatants of 37.27M with SK-MEL-28 cells cultured in fetal bovine serum-containing medium.

32-27M is an IgM antibody derived from LNL of a melanoma patient. It reacts with all melanoma, astrocytoma, and neuroblastoma cell lines, WI-38 fibroblasts, and sheep erythrocytes but not with cancer lines of epithelial origin. Despite this clear relation between neuroectodermal origin and antigen expression, the reactivity of 32-27M disappeared when cells were cultured in serum-free ITS medium in the absence of fetal bovine serum (Table 2). When fetal bovine serum was returned to the medium, partial recovery of 32-27M reactivity occurred after 6 hrs of incubation and full recovery of reactivity was observed after 24 hrs of incubation (FIG. 5). The antigen is heat-stable and neuraminidase-sensitive, suggesting an acidic glycolipid. In immunostaining, 32-27M reacted with a number of acidic glycolipids in sheep erythrocyte extracts (FIG. 3). It appears that neuroectodermally derived cells, but not most other cell types, incorporate this antigen from fetal bovine serum 2-39M is an IgM antibody derived from LNL of a melanoma patient. It does not react with any of the human cultured cell lines or human erythrocytes (Table 2). It agglutinates sheep erythrocytes and it reacted with an acidic glycolipid isolated from these cells in immunostaining (FIG. 3). EBV transformation and cell-fusion techniques represent distinct approaches to the isolation of human mAbs. Each method, as currently applied, combines certain advantages and certain limitations. For instance, easy clonability is an advantage with methods depending on hybrid formation (particularly NS-1 hybrids)

that is not achievable with EBV-transformed cells. However, there is a higher likelihood that antibody-secreting populations will be identified after EBV infection, because of the polyclonal proliferation of EBV-infected cells, than after the more stringent and inherently more random process of hybrid formation. By using these two approaches sequentially (31,32), the superior sampling characteristics of the EBV method may be combined with the superior clonability and growth characteristics of the NS-1 hybrid. However, the major problem in the use of this strategy is the loss of antibody-secreting cells during the initial expansion of the EBV-transformed cultures to obtain a sufficient number of cells for NS-1 fusion.

Several of the mAbs derived in this study identify antigens that exemplify the features of the three classes of antigens identified by autologous and allogeneic typing of human serum using conventional serological methods (2). The antigen recognized by GXM1 has the characteristic of a class 1 (unique) melanoma antigen, i.e., highly restricted expression to autologous melanoma cells. The availability of the mAb to a human class 1 antigen will facilitate the study of this class of antigen. The antigen detected by HJM1 has the characteristics of a class 2 melanoma antigen, i.e., expression by the autologous melanoma, and a subset of allogeneic melanomas, but not by cells of nonneuroectodermal origin. HJM1 reacts strongly with GD3 and reacts less strongly with GD2, two gangliosides that are widely expressed by neuroectodermal cells. Because individuals can develop humoral antibody against these normally occurring cell-surface components, we have termed this class of tumor antigen autoimmunogenic differentiation antigens (16). Irie and co-workers (21) have also isolated a human mAb produced by EBV-transformed cells that reacts with GD2, but its reactivity is restricted to GD2 and it does not show cross-reactivity with other gangliosides, as does HJM1. The antigens detected by FCM1 and DSM1 are classic examples of class 3 antigens. They are expressed by cells derived from diverse differentiation lineages but are not found on all cells from these sources or on all human cells.

It may be significant that autologous melanoma cells express low levels of antigen detected by HJM1 or FCM1. Immunoselections of stable antigen-negative or low-expressing tumor cell variants has been obtained in mice (33) and in humans (34) following passive administration of anti-ganglioside antibodies. It is contemplated that a similar process could occur as a consequence of an autologous humoral immune response.

References

1. Irie, R. F., Irike, K. & Morton, D. L. (1976) Cancer Res. 36, 3510–3517.
2. Old, L. J. (1981) Cancer Res. 41, 361–375.
3. Livingston, P. O., Shiku, H., Bean, M. A., Pinsky, C. M., Oettgen, H. F. & Old, L. J. (1979) Int. J. Cancer 24, 34–44.
4. Knuth, A. Danowsky, B. Oettgen, H. F. & Old, L. J. (1984) Proc. Natl. Acad. Sci. USA 81, 3511–3515.
5. Mukherji, B. & MacAlister, (1983) J. Exp. Med, 158, 240–245.
6. Anichini, A., Fossati, G. & Parmiani, G. (1985) Int. J. Cancer 35, 683–689.
7. Livingston, P. O., Old, L. J. & Oettgen, H. F. (1985) Monoclonal Antibodies and Cancer Therapy (Liss, New York), pp. 537–548.
8. Tai, T. Cahan, L. D., Tsuchida, T., Saxton R. E., Irie, R. F. & Morton, D. L. (1985) Int. J. Cancer 35, 607–612.
9. Bystryn, J. C., Jacobson, S. Harris, M., Roses, D., Speyer, J. & Levin, M. (1986) J. Biol. Response Modif. 5, 211–214.
10. Carey, T. E., Takahashi, T., Resnick, L. A., Oettgen, H. F. & Old, L. J. (1976) Proc. Natl. Acad, Sci. USA 73, 3278–3282.
11. Shiku, H., Takahashe, T., Oettgen, H. F. & Old, L. J. (1976) J. Exp. Med. 144, 873–881.
12. Takeyama, H., Shiku, H., Resnick, L. A., Houghton, A. N., Albino, A. P., Oettgen H. F. & Old, L. J. (1981) Proc. Am. Assoc. Cancer Res. 21, 300 (abstr.).
13. Albino, A. P., Lloyd, K. O., Houghton, A. N., Oettgen, H. F., & Old, L. J. (1981) J. Exp. Med. 154. 1764–1778.
14. Real, F. X., Mattes, M. J., Houghton, A. N., Oettgen, H. F. & Old, L. J. (1981) J. Exp. Med. 160, 1219–1233.
15. Carey, T. E., Lloyd, K. O., Takahashi, T., Travassos, L. & Old, L. J. (1979) Proc. Natl. Acad. Sci USA 76, 2898–2902.
16. Watanabe, T., Pukel, C. S. Takeyama, H., Lloyd, K. O., Shiku, H., Li, L. T. C., Travassos, L. R., Oettgen, H. F. & Old, L. J. (1982) J. Exp. Med. 156, 1884–1889.
17 Steinmetz, M., Klein, G., Koskimies, S. & Makel, O. (1977) Nature (London) 269, 420–422.
18. Engelman, E. G., Foung, S. K. H., Larrick, J. & Raubitschek, A. (1985) Human Hybridomas and Monoclonal Antibodies (Plenum, New York).
19. Houghton, A. N., Brooks, H., Cote, R. J., Taormina, M. C., Oettgen, H. F. & Old, L. J. (1983) J. Exp. Med. 158, 53–65.
20. Irie, R. F., Sze, L. L. & Saxton, R. E. (1982) Proc. Natl. Acad. Sci. USA 79, 5666–5670.
21. Cahan, J. D., Irie, R. F., Singh, R., Cassidenti, A. & Paulson, J. C. (1982) Proc. Natl. Acad. Sci. USA 79, 7629–7633.
22. Tai, T., Paulson, J. C., Cahan, L. D. & Irie, R. F. (1983) Proc. Natl. Acad. Sci. USA 80, 5392–5396.
23. Watson, D. B., Burns, G. F., & Mackay, I. R. (1983) J. Immunol. 130, 2442–2447.
24 Kan-Mitchell, J., Imam., A., Kempt, R. A., Taylor, C. R. & Mitchell, M. S. (1986) Cancer Res. 46, 2490–2496.
25. Cote, R. J., Morrissey, D. M., Houghton, A. N., Beattie, E. J., Jr., Oettgen, H. F. & Old, L. J. (1983) Proc. Natl. Acad. Sci. USA 80, 2026–2030.
26. Miller, G. & Lipman, M. (1983) Proc. Natl. Acad. Sci. USA 70, 190–194.
27. Dippold, W. G., Lloyd, K. O., Li., L. T. C., Oettgen, H. F. & Old, L. J. (1980) Proc. Natl. Acad. Sci. USA 77, 6114–6118.
28. Pukel, C. S., Loyd, K. O., Travassos, L. R., Dippold, W. G., Oettgen, H. G. & Old, L. J. (1982) J. Exp. Med. 155, 1133–1147.
29. Natoli, E. J., Livingston, P. O., Pukel, C. S., Lloyd, K. O., Weigandt, J., Szalay, J., Oettgen, H. F. & Old, L. J. (1986) Cancer Res. 46, 4116–4120.
30. Furukawa, K., Clausen, H., Hakomori, S., Sakamoto, J., Look, K., Lundblad, A., Mattes, M. J., & Lloyd, K. O. (1985) Biochemistry 24, 7820–7826.

31. Kozber, D., Roder, J. C., Chang, T. H. Stelplewski, A. & Koprowski, H. (1982) Hybridoma 1, 323–328.
32. Thompson, K. M., Melamed, K., Eagle, B. D., Gorick, T., Gibson, T., Holburn, A. H. & Hughes-Jones, N. C. (1986) Immunology 58, 157–160.
33. Young, W. W. & Hakomori, S. (1981) Science 211, 487–489.
34. Houghton, A. N., Mintzer, D., Cordon-Cardo, C., Welt, S., Fliegel, B., Vadhan, S., Carswell, E., Melamed, M. R., Oettgen, H. F. & Old, L. J. (1985) Proc. Natl. Acad. Sci. USA 82, 1242–1246.

What is claimed is:

1. The human monoclonal antibody produced by the hybridoma cell line designated GXM1.
2. The hybridoma cell line designated GXM1 which produces the monoclonal antibody of claim 1 and is deposited with the ATCC under Accession No. HB 9414.
3. The human monoclonal antibody produced by the hybridoma cell line designated HJM1.
4. The hybridoma cell line designated HJM1 which produces the monoclonal antibody of claim 3 and is deposited with the ATCC under Accession No HB 9416.
5. The human monoclonal antibody produced by the hybridoma cell line designated FCM1.
6. The hybridoma cell line designated FCM1 which produces the monoclonal antibody of claim 5 and is deposited with the ATCC under Accession No. HB 9417.
7. The human monoclonal antibody produced by the hybridoma cell line designated DSM1.
8. The hybridoma cell line designated DSM1 which produces the monoclonal antibody of claim 7 and is deposited with the ATCC under Accession No. HB 9418.
9. The monoclonal antibody of claim 1, 3, 5, or 7 labeled with a detectable moiety.
10. A method of in vivo melanoma diagnosis which comprises contacting a sample from a human subject with a monoclonal antibody of claim 15 under suitable conditions so as to form a complex between the monoclonal antibody and an antigen derived from the melanoma and detecting the complex so formed, thereby diagnosing melanoma in the subject.
11. A conjugate comprising a monoclonal antibody of claim 1, 3, 5 or 7 attached to a cytotoxic tumor agent.
12. A therapeutic composition comprising an effective melanoma growth inhibiting amount of the conjugate of claim 11 and a pharmaceutically acceptable carrier.
13. A therapeutic composition of claim 12, wherein the growth inhibiting amount is an amount sufficient to kill the melanoma
14. A therapeutic composition comprising an effective melanoma growth inhibiting amount of the monoclonal antibody of claim 1, 3, 5 or 7 and a pharmaceutically acceptable carrier.

* * * * *